United States Patent
Kappel et al.

(10) Patent No.: US 9,700,345 B2
(45) Date of Patent: Jul. 11, 2017

(54) SNARE WITH RETRACTABLE ENGAGING MEMBERS

(75) Inventors: Gary Kappel, Acton, MA (US); Larry Stanton, Burlington, MA (US); Ruth Cheng, Natick, MA (US); Ken Keene, Winchester, MA (US); Gerald Heller, Bedford, MA (US); Man Nguyen, West Roxbury, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1068 days.

(21) Appl. No.: 13/328,006

(22) Filed: Dec. 16, 2011

(65) Prior Publication Data

US 2012/0172662 A1 Jul. 5, 2012

Related U.S. Application Data

(60) Provisional application No. 61/428,263, filed on Dec. 30, 2010.

(51) Int. Cl.
*A61B 17/26* (2006.01)
*A61B 17/221* (2006.01)
(Continued)

(52) U.S. Cl.
CPC ...... *A61B 17/32056* (2013.01); *A61B 17/221* (2013.01); *A61B 18/1492* (2013.01);
(Continued)

(58) Field of Classification Search
CPC .... A61B 2018/1405; A61B 2018/1407; A61B 2018/141; A61B 2018/142;
(Continued)

(56) References Cited

U.S. PATENT DOCUMENTS 4,905,691 A 3/1990 Rydell
5,279,539 A * 1/1994 Bohan et al. .................. 600/37
(Continued)

FOREIGN PATENT DOCUMENTS

JP 2000271146 A * 10/2000
JP 2001258892 A * 9/2001
(Continued)

OTHER PUBLICATIONS

English Translation of JP2000271146.*
(Continued)

*Primary Examiner* — Melanie Tyson
*Assistant Examiner* — Erin Colello
(74) *Attorney, Agent, or Firm* — Bookoff McAndrews, PLLC

(57) ABSTRACT

A snare for retrieving foreign objects within the body of a patient including a hollow elongate tubular member comprising an inner surface and an outer surface and a lumen defined by the inner surface, a proximal end and a distal end, the hollow elongate tubular member forms a loop at the distal end, the loop having an open position and a closed position, the loop comprising at least one opening and a wire slidably disposed in the lumen of the elongate tubular member, the wire comprising at least one engaging member for engaging tissue, the at least one engaging member extends through the at least one opening in the hollow elongate tubular member when the wire is in a first position and the at least one engaging member retracts into the lumen of the elongate tubular member when the wire is moved to a second position.

22 Claims, 7 Drawing Sheets

(51) Int. Cl.

| | | |
|---|---|---|
| *A61B 17/3205* | (2006.01) | |
| *A61B 18/14* | (2006.01) | |
| *A61B 17/32* | (2006.01) | |
| *A61B 18/00* | (2006.01) | |
| *A61B 17/00* | (2006.01) | |

(52) U.S. Cl.
CPC ........... *A61B 2017/00269* (2013.01); *A61B 2017/320064* (2013.01); *A61B 2018/00601* (2013.01); *A61B 2018/141* (2013.01)

(58) Field of Classification Search
CPC  A61B 2018/00273; A61B 2018/00279; A61B 2018/1475; A61B 18/149; A61B 2018/00267; A61B 18/1492; A61B 2018/00601; A61B 2017/00269; A61B 2017/320064; A61B 17/32056; A61B 17/221; A61B 17/22; A61B 2017/22017; A61B 17/22031; A61B 2017/2212; A61B 2017/2215; A61B 2017/2217; A61M 2025/0096

See application file for complete search history.

(56) References Cited

U.S. PATENT DOCUMENTS

| | | | |
|---|---|---|---|
| 5,376,094 A | 12/1994 | Kline | |
| 5,417,697 A * | 5/1995 | Wilk et al. | 606/113 |
| 5,437,665 A * | 8/1995 | Munro | 606/47 |
| 5,480,404 A * | 1/1996 | Kammerer et al. | 606/113 |
| 5,554,163 A * | 9/1996 | Shturman | 606/159 |
| 5,575,694 A | 11/1996 | Hawkins et al. | |
| 5,759,187 A * | 6/1998 | Nakao et al. | 606/114 |
| 5,782,839 A * | 7/1998 | Hart et al. | 606/113 |
| 5,782,840 A * | 7/1998 | Nakao | 606/114 |
| 5,846,248 A | 12/1998 | Chu et al. | |
| 5,961,526 A | 10/1999 | Chu et al. | |
| 5,997,547 A * | 12/1999 | Nakao et al. | 606/114 |
| 6,006,755 A * | 12/1999 | Edwards | A61B 18/00 128/898 |
| 6,007,546 A * | 12/1999 | Snow et al. | 606/113 |
| 6,010,512 A | 1/2000 | Chu et al. | |
| 6,036,698 A * | 3/2000 | Fawzi et al. | 606/114 |
| 6,050,995 A | 4/2000 | Durgin | |
| 6,063,082 A * | 5/2000 | DeVore et al. | 606/45 |
| 6,064,082 A * | 5/2000 | Kawai | H01L 29/7783 257/191 |
| 6,123,665 A * | 9/2000 | Kawano | 600/104 |
| 6,162,209 A * | 12/2000 | Gobron et al. | 606/1 |
| 6,190,384 B1 | 2/2001 | Ouchi | |
| 6,210,416 B1 * | 4/2001 | Chu et al. | 606/113 |
| 6,221,039 B1 | 4/2001 | Durgin et al. | |
| 6,235,026 B1 | 5/2001 | Smith | |
| 6,258,087 B1 * | 7/2001 | Edwards | A61B 18/12 600/374 |
| 6,287,304 B1 * | 9/2001 | Eggers et al. | 606/37 |
| 6,309,399 B1 | 10/2001 | Barbut et al. | |
| 6,383,183 B1 * | 5/2002 | Sekino et al. | 606/34 |
| 6,488,673 B1 * | 12/2002 | Laufer | A61B 18/00 604/516 |
| 6,517,539 B1 | 2/2003 | Smith et al. | |
| 6,537,273 B1 * | 3/2003 | Sosiak et al. | 606/41 |
| 6,540,695 B1 * | 4/2003 | Burbank et al. | 600/564 |
| 6,602,262 B2 | 8/2003 | Griego et al. | |
| 6,610,056 B2 | 8/2003 | Durgin et al. | |
| 6,743,228 B2 * | 6/2004 | Lee et al. | 606/47 |
| 6,761,717 B2 | 7/2004 | Bales et al. | |
| 6,773,432 B1 * | 8/2004 | Clayman et al. | 606/41 |
| 6,944,490 B1 * | 9/2005 | Chow | A61B 18/1492 600/374 |
| 6,972,017 B2 | 12/2005 | Smith et al. | |
| 7,052,495 B2 | 5/2006 | Smith | |
| 7,198,635 B2 * | 4/2007 | Danek | A61N 1/403 606/41 |
| 7,214,180 B2 * | 5/2007 | Chin | A61B 17/00008 600/37 |
| 7,270,663 B2 * | 9/2007 | Nakao | 606/47 |
| 7,276,067 B2 | 10/2007 | Bales et al. | |
| 7,507,200 B2 * | 3/2009 | Okada | 600/104 |
| 7,588,580 B2 * | 9/2009 | Okada | 606/113 |
| 7,727,249 B2 | 6/2010 | Rahmani | |
| 7,789,881 B2 | 9/2010 | Weitzner | |
| 8,157,811 B2 * | 4/2012 | Shinozuka et al. | 606/113 |
| 2003/0139750 A1 * | 7/2003 | Shinozuka | A61B 17/221 606/113 |
| 2003/0233099 A1 * | 12/2003 | Danaek et al. | 606/96 |
| 2004/0092953 A1 * | 5/2004 | Salameh et al. | 606/113 |
| 2004/0158127 A1 * | 8/2004 | Okada | 600/127 |
| 2004/0186512 A1 * | 9/2004 | Bruckheimer et al. | 606/200 |
| 2005/0085808 A1 * | 4/2005 | Nakao | 606/47 |
| 2005/0154378 A1 * | 7/2005 | Teague | A61B 17/221 606/2.5 |
| 2006/0047279 A1 | 3/2006 | Smith et al. | |
| 2006/0058813 A1 * | 3/2006 | Teague | A61B 17/32056 606/113 |
| 2006/0178658 A1 | 8/2006 | Smith | |
| 2006/0253128 A1 * | 11/2006 | Sekine et al. | 606/139 |
| 2008/0009883 A1 | 1/2008 | Bieneman | |
| 2008/0221587 A1 * | 9/2008 | Schwartz | 606/113 |
| 2008/0242934 A1 | 10/2008 | Skerven et al. | |
| 2009/0131749 A1 * | 5/2009 | Ahmed et al. | 600/106 |
| 2009/0306678 A1 * | 12/2009 | Hardert et al. | 606/127 |
| 2010/0036375 A1 | 2/2010 | Regadas | |
| 2013/0131688 A1 * | 5/2013 | Schwartz | 606/113 |

FOREIGN PATENT DOCUMENTS

| | | | |
|---|---|---|---|
| JP | 2001276081 A | * | 10/2001 |
| WO | 2005034774 | | 4/2005 |
| WO | 2008044615 | | 4/2008 |

OTHER PUBLICATIONS

English Translation of JP2001258892.*
English Translation of JP2001276081.*
http://www.bostonscientific.com/Device.bsci?page=HCP_Overview&navReiid=1000.1003&method=DevDetailHCP&id=10074592&pageDisclaimer=Disclaimer.ProductPage, Mar. 15, 2012.
http://www.bostonscientific.com/templatedata/imports/collateral/Endoscopy/oth_gastrolist_01_us.pdf, 2008.
http://www.bostonscientific.com/procedure/ProcedureLanding.bsci/,/navRelId/1000.1002/method/Procedure/id/10001211/attributeTypeId/1/seo.serve, 2012.
http://www.bostonscientific.com/procedure/ProcedureLanding.bsci/,/navRelId/1000.1002/method/PRODUCTS/id/10001211/seo.serve, 2012.
Priority U.S. Appl. No. 61/428,263, filed Dec. 30, 2010; Inventors: Kappel et al.

* cited by examiner

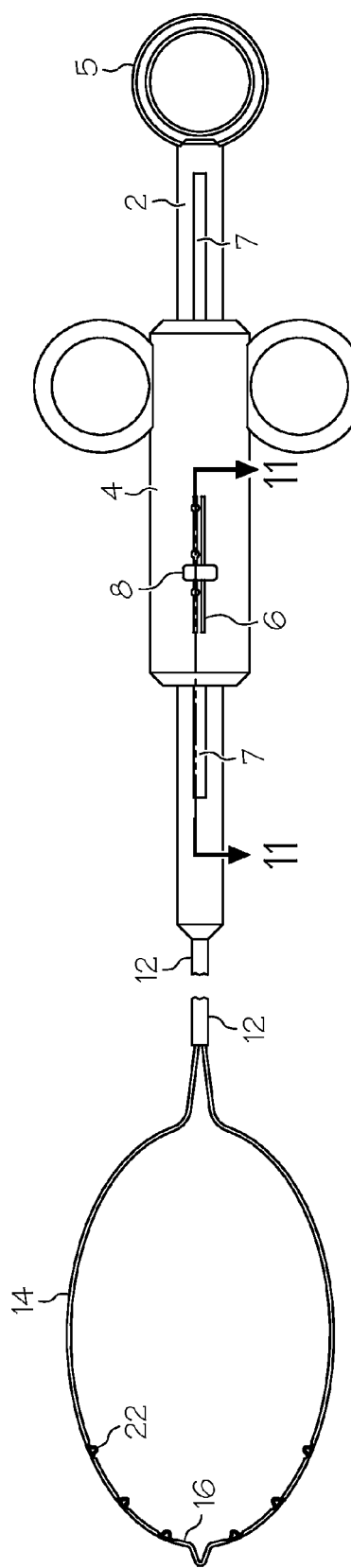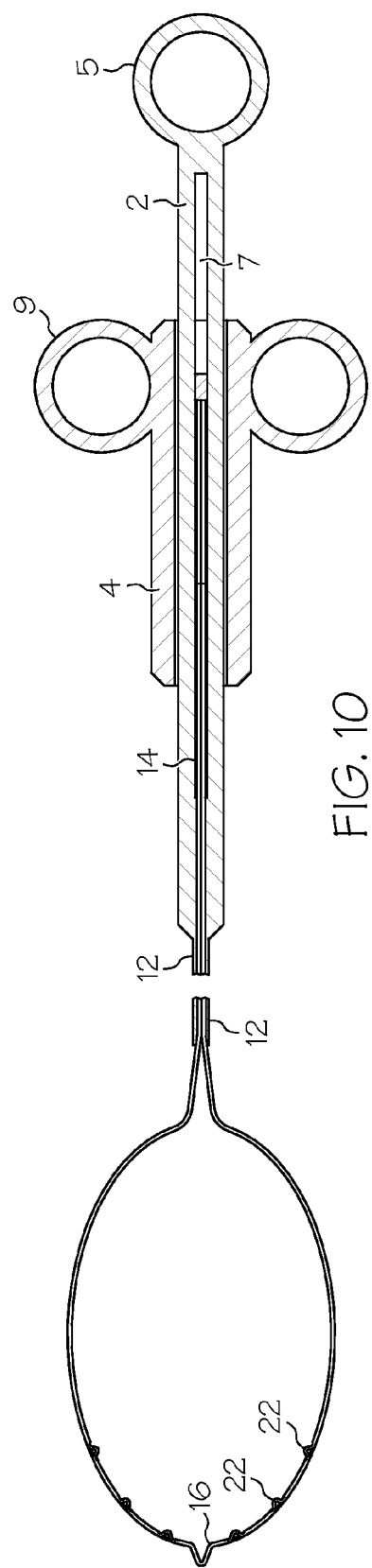
FIG. 9
FIG. 10

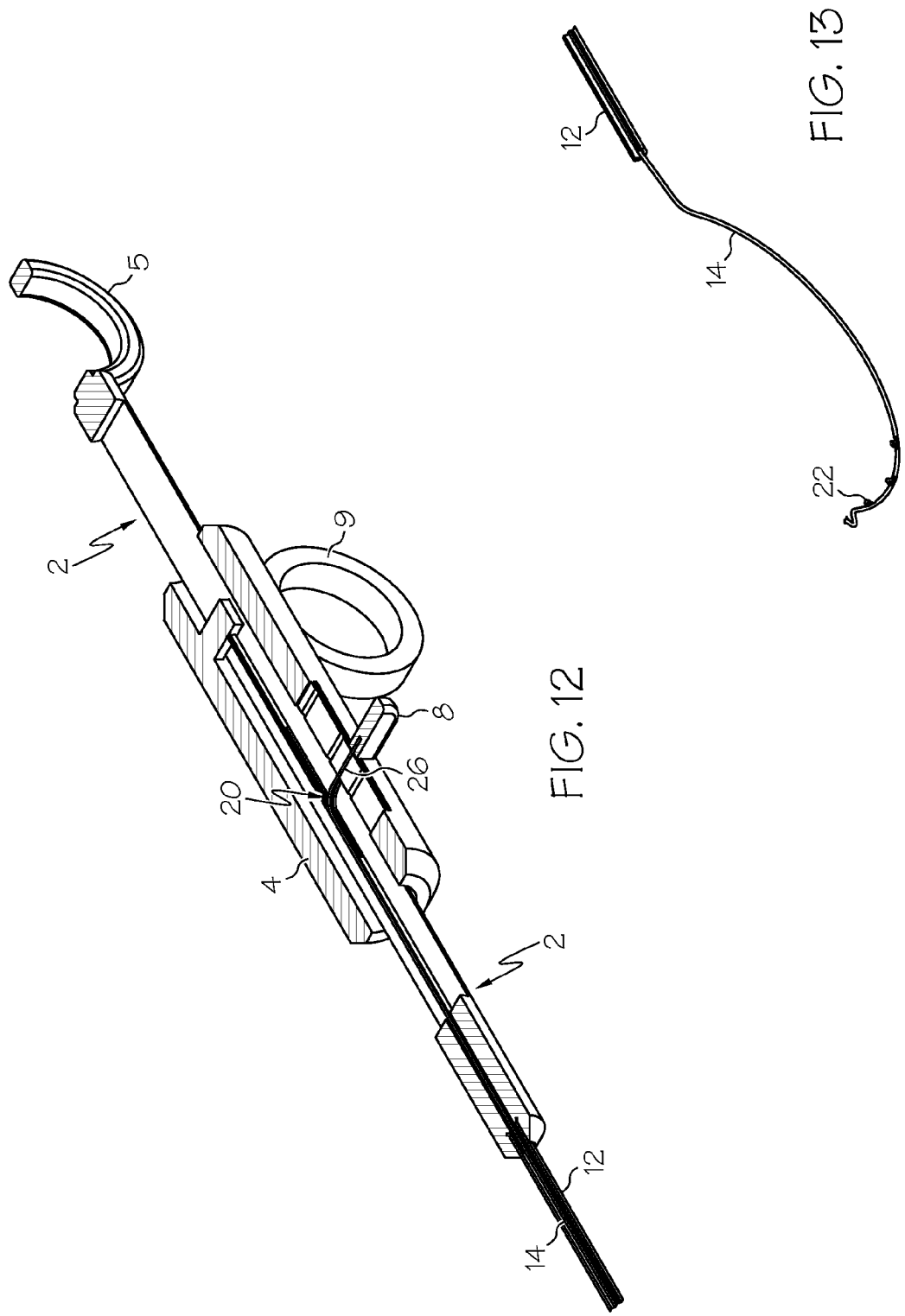

SNARE WITH RETRACTABLE ENGAGING MEMBERS

CROSS-REFERENCE TO RELATED APPLICATIONS

This application claims priority to U.S. Patent Provisional Application No. 61/428,263 filed Dec. 30, 2010, the entire contents of which are hereby incorporated herein by reference.

BACKGROUND OF THE INVENTION

The invention relates generally to a medical device, and more particularly to a medical retrieval device for capturing and/or removing objects from within a body cavity.

Medical retrieval devices or snares are used to remove objects from body lumens by inserting the retrieval device, typically by way of a catheter assembly, into the body lumen to the retrieval site, engaging the object to be retrieved, and removing the object from the body lumen.

Objects which are removed from body lumens include, for example, blood clots, plaque, kidney stones, gall stones, polyps, dysplastic tissue, cancerous lesions and so forth.

Common applications for medical snares include removal of objects from the lower gastrointestinal tract such as the colon and rectum, esophagus, stomach and for mucosal resection generally and polypectomy generally, etc.

One application for which the device is particularly suited is for endoscopic mucosal resection in the lower gastrointestinal tract wherein dysplastic or cancerous lesions are identified, margins are noted and advancing the snare through the body, positioning the snare and the lesion and capturing the lesion within the snare. Other steps may be included in the procedure.

There remains a need in the art for a snare having superior means of gripping and removing objects from a patient's body.

SUMMARY OF THE INVENTION

In one aspect, the present invention relates to a snare for retrieving foreign objects within the body of a patient, the snare including a hollow elongate tubular member comprising an inner surface and an outer surface and a lumen extending therethrough and defined by the inner surface of the hollow elongate tubular member, a distal end and a proximal end, the hollow elongate tubular member forms a loop at the distal end, the loop comprising at least one opening, the loop having an open position and a closed position, and a wire slidably disposed in the lumen of the elongate tubular member, the wire comprising at least one engaging member for engaging tissue, said at least one engaging member extends through one of said at least one opening when the wire is in a first position and at least one engaging member retracts into the lumen of the elongate tubular member when the wire is in a second position.

In one embodiment, the present invention relates to a snare for retrieving foreign objects within the body of a patient, the snare including a sheath extending from a proximal end which, in an operative position, is located outside the body, to a distal end which, in the operative position is located within the body, the sheath having an outer surface and an inner surface, the inner surface defining a lumen; a hollow elongate tubular member disposed within the lumen of the sheath, the hollow elongate tubular member comprising an inner surface and an outer surface and a lumen defined by the inner surface, a proximal end and a distal end, the hollow elongate tubular member forming a loop at the distal end, the loop comprising at least one opening, the loop having an open position and a closed position; and a wire slidably disposed in the lumen of the elongate tubular member, the distal end of the wire comprising at least one engaging member for engaging tissue, the wire having a first position and a second position within the hollow elongate tubular member wherein when the wire is in the first position the at least one engaging member extends out of the at least one opening in the hollow elongate tubular member and when the wire is in the second position, the at least one engaging member is retracted within the lumen of the hollow elongate member.

In one embodiment, the present invention relates to a snare for retrieving foreign objects within the body of a patient including a first handle portion, a sheath having a proximal end and a distal end and an inner surface and an outer surface, the inner surface defining a lumen, the sheath engaged to the first handle portion at the proximal end, the distal end in an operative position is located inside the body of a patient and the proximal end is located outside the body of the patient, a second handle portion slidably engaged with the first handle portion, the second handle portion having a first position and a second position, a hollow elongate tubular member comprising an inner surface and an outer surface and a lumen defined by the inner surface, a proximal end and a distal end, the distal end of the hollow elongate tubular member forming a loop at the distal end, the loop comprising at least one opening, the loop having an open position and a closed position, the hollow elongate tubular member extending through the lumen of the sheath, the hollow elongate tubular member is engaged to the second handle portion and when the second handle portion is in the first position, the hollow elongate tubular member is disposed entirely within the sheath, when the second handle portion is in the second position, the loop of the hollow elongate tubular member extends from the distal end of the sheath, a third handle portion slidably engaged with the second handle portion, the third handle portion having a first position and a second position and a wire slidably disposed in the lumen of the elongate tubular member, the wire comprising at least one engaging member for engaging tissue, the wire having a proximal end and a distal end, the wire comprising at least one engaging member at distal, the wire is engaged to the handle at the proximal end, when the handle is in a first position, the at least one engaging member extends through the at least one opening when the wire is in a first position and the at least one engaging member retracts into the lumen of the elongate tubular member when the handle is moved to a second position.

These and other aspects, embodiments and advantages of the present disclosure will become immediately apparent to those of ordinary skill in the art upon review of the Detailed Description and Claims to follow.

BRIEF DESCRIPTION OF THE DRAWINGS

FIG. 9 is a snare similar to that shown in FIG. 1 showing the distal end and the proximal end of the device.

FIG. 10 is a longitudinal cross-sectional view of a device similar to that shown in FIGS. 1 and 9 wherein the proximal end and the distal end are shown.

FIG. 12 is a partial perspective view of the proximal end of the device illustrating the handle portion and the sliding mechanism for moving the inner wire of the snare to move the engaging members in and out of the openings in the loop of the snare.

FIG. 13 is a partial perspective view of the distal end of the outer wire disposed within a sheath at the proximal end and at the distal end having barbs of the inner wire extending through openings in the outer wire.

DETAILED DESCRIPTION OF THE INVENTION

Figure 1:
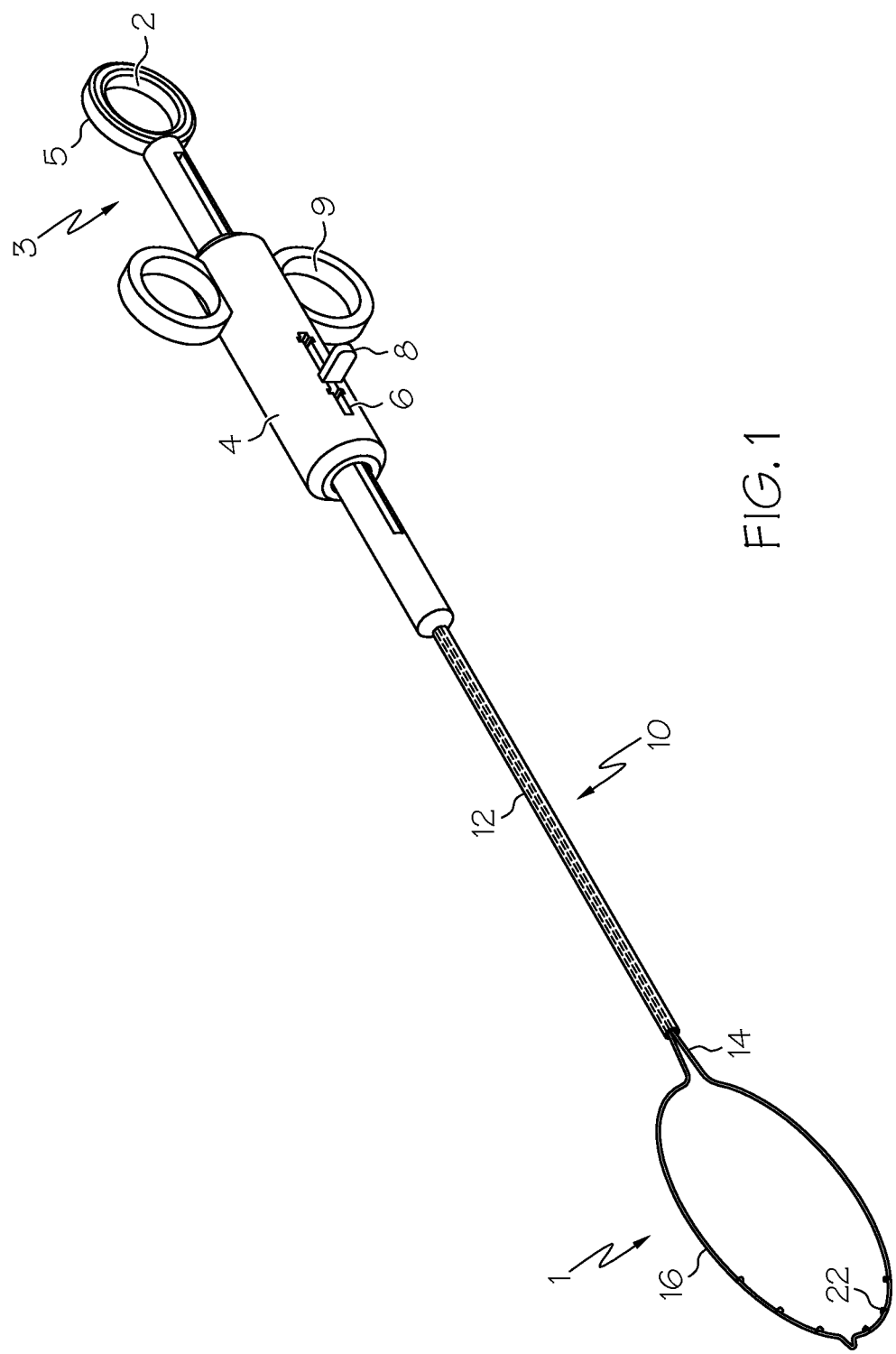
FIG. 1 illustrates generally at 10 one embodiment of a snare according to the invention.
Figure 3:
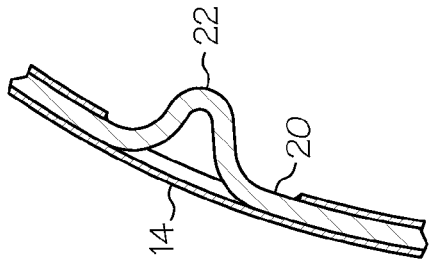
FIG. 3 is a close up view of a barb extending through an opening of the outer wire of the loop according to the invention.

While embodiments of the present disclosure may take many forms, there are described in detail herein specific embodiments of the present disclosure. This description is an exemplification of the principles of the present disclosure and is not intended to limit the disclosure to the particular embodiments illustrated.

As shown in the drawings and described throughout the following description, as is traditional when referring to relative positioning on an object, the term "proximal" refers to the end of the apparatus that is closer to the user and the term "distal" refers to the end of the apparatus that is further from the user. The distal end in the operative position is located within the patient's body and the proximal end in the operative position is located outside the patient's body.

Figure 4:
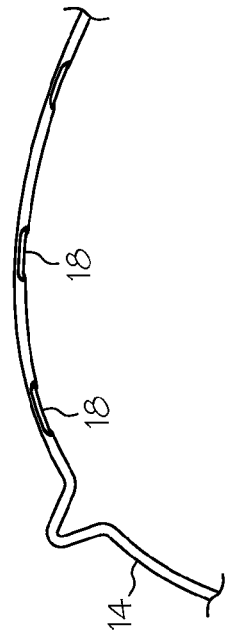
FIG. 4 is a partial view of the outer wire of the loop wherein the openings through which engaging members extend are clearly visible.

Turning now to the drawings, FIG. 1 illustrates generally at 10, one embodiment of a snare according to the invention. Snare 10 includes a distal end 1 and a proximal end 3. Proximal end 3 includes a first handle portion 2 having a single finger loop 5, a second handle portion 4 with a double finger loop 9, and a third handle portion 8. First handle portion 2 is coupled to sheath 12. Second handle portion 4 is coupled to a hollow outer wire 14, the distal end of which has a loop 16. It should be noted that the hollow outer wire 14 doubles back the second handle portion 4. The loop 16 has an open position and a closed position. When loop 16 is in its closed position it can grip and hold tissue. The loop portion 16 of snare 10 has openings 18 therein best seen in FIG. 4. First handle portion 2 includes a slot 7 within which second handle portion 4 is slidably received and can be moved distally or proximally to deploy or retract loop 16 of snare 10. Refer also to FIG. 9 and FIG. 10 which is a cross-sectional view showing the same.

The slot 7 for the second handle portion 4 may further optionally include variable position capability, for example, including snap-in/snap-out detents for extending or retracting the length of the hooks, barbs or needles from minimal engagement with the tissue to greater engagement of the tissue depending on the grasping requirements, tissue density, etc.

Figure 5:
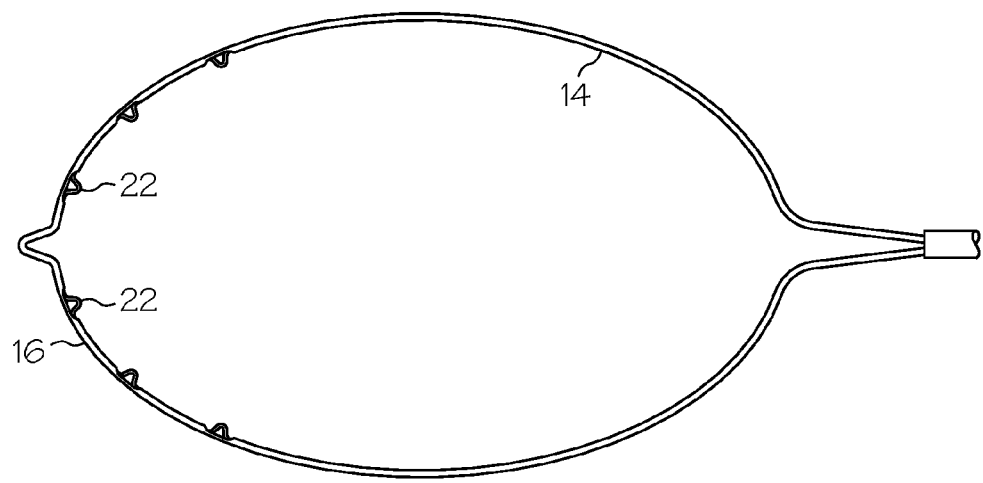
FIG. 5 illustrates an alternative embodiment of the loop having an open configuration rather than being a closed loop.

Optionally, loop 16 may be an open loop as shown in FIG. 5.

While in these embodiments, the snare is shown having an oval shape it is not limited as such. The snare may have a round or elliptical shape, may be angular, and may have multiple lobes, for example.

Outer wire 14 may be formed from any suitable metal including stainless steel 302, 304, 17-4, 17-4 ph, shape memory metals or superelastic metals including Nitinol Ni—Ti alloy, ELGILOY® Co—Cr—Ni alloy, as well as suitable polymer materials, etc.

Figure 2:
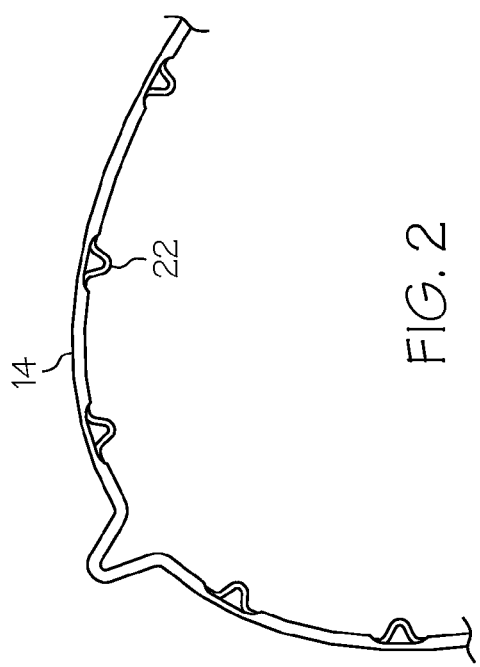
FIG. 2 is a partial view of a loop similar to that shown in FIG. 1 with barbs extended through the openings in the outer wire of the loop.
Figure 6:
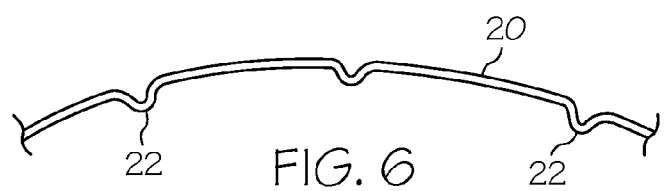
FIG. 6 is a partial view of an embodiment of the inner wire of the loop wherein the barbs are clearly illustrated.
Figure 7:
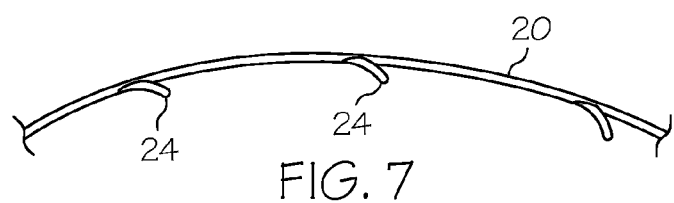
FIG. 7 is a partial view of an alternative embodiment of the inner wire of the loop wherein hooks are shown as an alternative to the barbs shown in FIG. 6.
Figure 8:
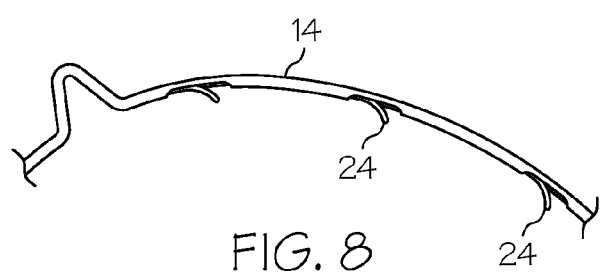
FIG. 8 is a partial view of the loop wherein hooks similar to those shown in FIG. 6 are extending through the outer wire of the loop.

Snare 10 also includes an inner wire 20 slidably disposed within outer wire 14. Inner wire 20, a partial view of which is shown in FIG. 6, has engaging members, in this embodiment, barbs 22. In an alternative embodiment illustrated in FIGS. 7 and 8, inner wire 20 has hooks 24. FIGS. 2 and 8 are partial enlarged views of a portion of loop 16 wherein the barbs 22 or hooks 24 are shown extended through openings 18 in outer wire 14.

Inner wire 20 may be formed from any flexible metal including stainless steel, shape memory or superelastic metals including Ni—Ti alloys and Co—Cr—Ni alloys., etc. In one embodiment, inner wire 20 is formed from a flexible metal such as, for example, Nitinol. The barbs or hooks can be made from the same material as the wire or may be made from a different material such as a polymeric material. For example, polymeric snaps may be attached to the metal wire via any suitable fabrication process such as injection molding for example. Wires of the type described herein are available from Fort Wayne Metals in Fort Wayne, Ind. For example, a Helical Hollow Strand® (HHS) having an inside diameter of 0.0001" (0.0254 mm), an outside diameter of 0.0025" (0.0635 mm) and a filar diameter of 0.0005" (0.0127 mm) can be used. This hollow strand tubing is flexible and kink resistant and can be tailored to customer specifications for stiffness, flexibility, compression, tension, lubricity, tracking, responsiveness, etc. Metal tubing of this type is also commercially available from Asahi Intecc headquartered in Aichi Japan.

These materials are intended for illustrative purposes only and not as a limitation on the scope of the present invention. Other materials, designs, manufacturing processes, etc. can be employed herein. For example, tubing with laser cut slits on the outside of the snare shape could aid in the flexing of the tube.

Figure 11:
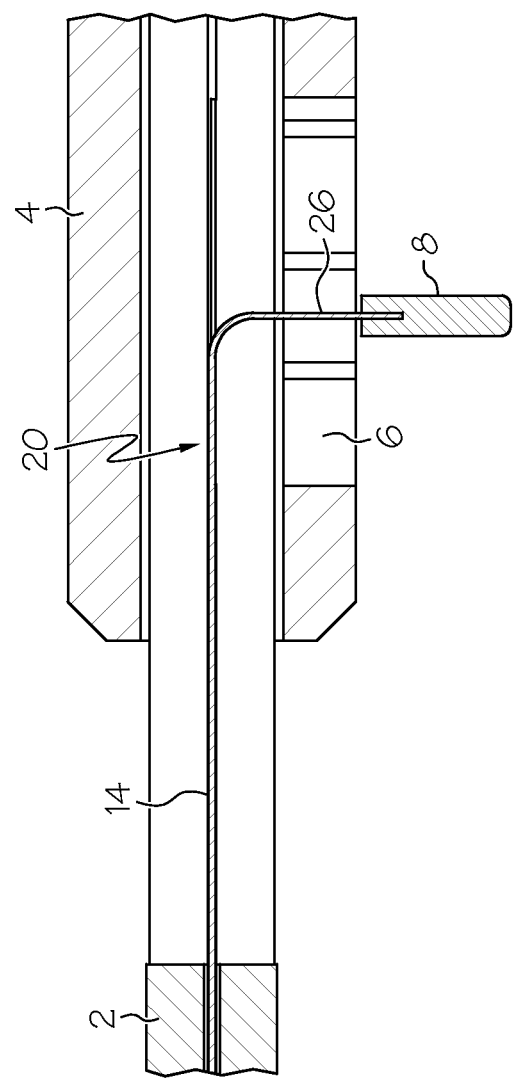
FIG. 11 is a cross-sectional view taken at section 11-11 in FIG. 9.
Figure 12A:
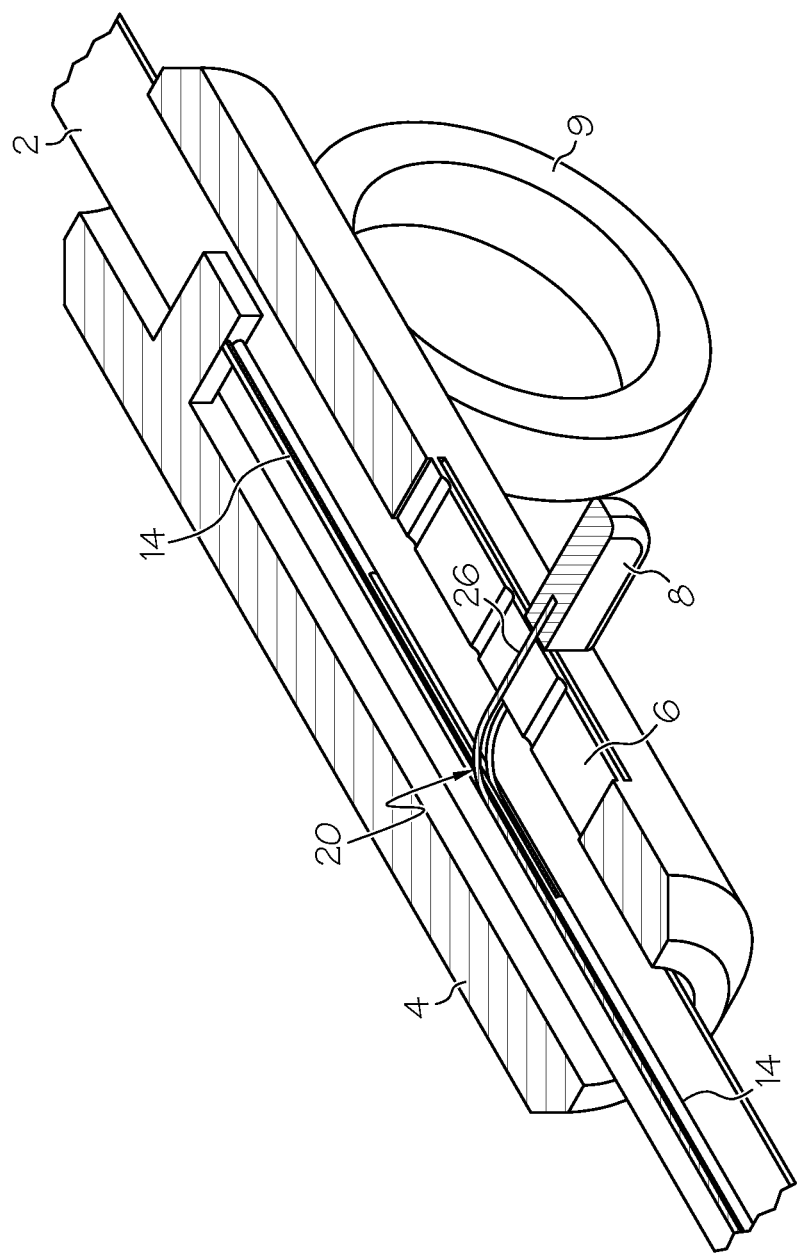
FIG. 12A is an enlarged view of FIG. 11 to clearly illustrate the attachment of the inner wire to the secondary slide handle portion.

Third handle portion 8 is coupled to a pull wire 26 which is slidably disposed within slot 6 of second handle portion 4. Inner wire 20 includes a section referred to herein as the pull wire 26 which is mechanically connected to handle 8 best seen in FIGS. 11, 12, 12A and 12 such as by insert molding, bonding, press fitting or other suitable method. Pull wire 26 can also be connected via additional parts such as connector shafts or bars, plastic extensions and so forth. FIG. 12A also clearly illustrates the attachment of the outer wire 14 to second handle portion 4.

When the handle 8 and pull wire 26 are shifted from a first position to a second position, inner wire 20 moves and the barbs 22 or hooks 24 of inner wire 20 extend or retract through openings 18 in outer wire 14. Barbs 22 or hooks 24 can engage tissue when extended through openings 18 of outer wire 14.

For example, when handle portion 8 is moved distally causing the inner wire 20 to move in the distal direction, barbs 22 or hooks 24 of inner wire 20 extend through the openings 18 in outer wire 14. When handle portion is moved proximally, barbs 22 or hooks 24 are retracted back inside of outer wire 14. Alternatively, the device can be configured so that the barbs 22 or hooks 24 are extended when the inner wire 20 is pulled by handle 8 and pull wire 26 in the proximal direction and retracted when the inner wire 20 is pushed in the distal direction.

Snare 10 is used to retrieve objects from body cavities including organs, vessels, passages and orifices during a medical procedure by capturing or otherwise engaging the object to be retrieved using loop 16. The snare is manipulated by a user performing the medical procedure using to position the loop 16 relative to the object to be retrieved. The snare 10 can be used to retrieve objects from the body, for example, polyps or other abnormal tissue.

One specific procedure that the present invention finds utility in is for endoscopic mucosal resection (EMR) in the lower gastrointestinal tract (colon or rectum) for removal of polyps or other cancerous or abnormal tissue.

This procedure involves identification of dysplasia and making note of the margins. A solution is then injected into the submucosal layer under the lesion using a scleral needle, for example, to lift the mucosa. The snare 10 is then advanced through a working lumen of an endoscope towards the lesion. Once at the site of interest, snare 10 is deployed via second handle portion 4 by moving handle portion 4 from a first position to a second position by sliding movement through slot 7 of first handle portion (refer to FIG. 8) and loop 16 is placed flat over the lesion or area of resection. Retractable barbs 22 or hooks 24 or inner wire 20 are then deployed through the openings 18 in the outer wire 14 via third handle portion 8 and pull wire 26 which are slid through slot 6 in second (refer to FIGS. 8, 10, 11 and 11A). Loop 16 is then closed to capture the lesion within the snare 10. Optionally, the mobility of the tissue captured in snare 10 can be checked to make sure that no muscularis has been perforated.

Barbs 22 or hooks 24 are advantageous for consistent tissue capture within the snare. Once the tissue has been captured, barbs 22 or hooks 24 can be retracted by moving the handle portion 8 and pull wire section 26 from the second position back to the first position whether the movement is distal or proximal. The hooks 22 or barbs 24 could be positioned around the linearly length of the snare loop 16 at the distal half-end or the proximal half-end or on only one side or on the entire length of the loop 16. The frequency, spacing and pitch can be optimized depending on the grasping requirements as well. The hooks 22 or barbs 24 can also be placed around the snare loop outer wire diameter, for example, in four places around the outer diameter approximately 90° apart from one another.

Furthermore, the barbs or hooks may be sharpened to help resection.

Electrocautery may be applied to cut and resect the tissue captured within the snare 10. Barbs 22 or hooks 24 can also be retracted after electrocautery.

In electrocautery, the tissue is heated by a high frequency electrical current with a probe heated by direct current as a means of cutting, dissecting, coagulating, or fulgurating tissue. The frequency range is typically about 30 KHz to 1 MHz is and power is about 300 watts. See for example, U.S. Pat. Nos. 6,190,384 and 6,383,183, each of which is incorporated by reference herein in its entirety. The electrocautery probe may be delivered through the same endoscope or catheter as the snare, or may be delivered by itself through the body lumen as well. These ranges are intended for illustrative purposes and not as a limitation on the scope of the present invention. Other frequencies and power may be used in conjunction with the device disclosed herein without deviating from the scope of the present invention.

Electrosurgery, on the other hand, employs alternating current to directly heat the tissue operating in the radio frequency (RF) range of about 100 kHz to 5 MHz. Snare 10 may be used for mucosal resection or polypectomy generally as well.

Capturing and cauterizing polyps or other tissue is often referred to in the art as "hot biopsy". The Radial Jaw® 3 Biopsy Forceps commercially available from Boston Scientific Corp. can be employed to collect tissue endoscopically for histologic examination and may be used through an endoscope to cauterize and remove polyps and/or tissue specimens throughout the alimentary tract.

Another example of a snare of this type is the Captivator® II Snare and the Sensation™ Short Through Snare both of which are also commercially available from Boston Scientific Corp. and which are useful for removal and cauterization of diminutive polyps, sessile polyps and pedunculated polyps.

Other examples include the Rotatable snare for electrosurgical removal and cauterization of gastrointestinal tract polyps through an endoscope and the Twister™ Rotatable Polyp and Foreign Body Retrieval device which has a three dimensional wire basket that is fully rotatable and designed to facilitate polyp retrieval.

The engaging members may be added to any type of snare, basket or net type retrieval device.

Hot snares may be powered by electrosurgical generators such as the Endostat™ III Generator commercially available from Boston Scientific Corp. This generator is designed to have both bipolar and monopolar electrosurgical capability.

For hot snares see U.S. Pat. Nos. 5,376,094, 5,575,694, 5,846,248, 6,007,546, 6,010,512, 6,050,995 and 6,517,539, each of which is incorporated by reference herein in its entirety.

The energy may be focused on the combination of the outer wire 14 and the inner wire 20 or just on the inner wire 20, for example, and the outer wire 14 could be optionally an insulated outer wire 14.

While in specific embodiments illustrated herein snare 10 is delivered with an endoscope to the treatment site, other means can be employed as well including, for example, a catheter assembly, or by itself through a body lumen.

The description provided herein is not to be limited in scope by the specific embodiments described which are intended as single illustrations of individual aspects of certain embodiments. The methods, compositions and devices described herein can comprise any feature described herein either alone or in combination with any other feature(s) described herein. Indeed, various modifications, in addition to those shown and described herein, will become apparent to those skilled in the art from the foregoing description and accompanying drawings using no more than routine experimentation. Such modifications and equivalents are intended to fall within the scope of the appended claims.

All publications, patents and patent applications mentioned in this specification are herein incorporated by reference in their entirety into the specification to the same extent as if each individual publication, patent or patent application was specifically and individually indicated to be incorporated herein by reference. Citation or discussion of a reference herein shall not be construed as an admission that such is prior art.

The invention claimed is:

1. A snare for retrieving foreign objects within the body of a patient, the snare comprising:
    a hollow elongate tubular member comprising an inner surface, an outer surface, a lumen defined by the inner surface, a distal end, and a proximal end, wherein the hollow elongate tubular member forms a loop at the distal end, the loop comprising at least one opening, and the loop having an open position and a closed position; and
    a wire slidably disposed in the lumen of the elongate tubular member, the wire comprising at least one engaging member for engaging tissue, wherein the at least one engaging member extends through the at least one opening when the wire is in a first position, and wherein the at least one engaging member is retractable into the lumen of the elongate tubular member when the wire is moved to a second position.

2. The snare of claim 1 wherein said wire is a Nitinol wire.

3. The snare of claim 1 wherein said elongate tubular member comprises stainless steel.

4. The snare of claim 1 wherein said at least one engaging member is in the form of hooks, barbs or needles.

5. The snare of claim 1 wherein said loop comprises an open loop or a closed loop configuration.

6. The snare of claim 1 further comprising a sheath extending from a proximal end which, in an operative position, is located outside the body, to a distal end which, in the operative position is located within the body, the sheath having an outer surface and an inner surface, the inner surface defining a lumen, the proximal end of the hollow elongate tubular member is in communication with a first actuator for moving the hollow elongate tubular member from a position wherein the loop of the hollow elongate tubular member is covered by the distal end of the sheath to a position wherein the loop of the hollow elongate tubular member is extended beyond the distal end of the sheath.

7. The snare of claim 6 comprising a second actuator coupled to a proximal end of the wire, the second actuator having a first position and a second position, wherein when the second actuator is in its first position, the wire is in its first position, and the at least one engaging member extends through said at least one opening in said hollow elongate tubular member, and wherein when the second actuator is in its second position, the wire is in its second position, and the at least one engaging member is retracted into the lumen of the elongate tubular member.

8. The snare of claim 7 wherein the sheath is fixedly engaged to a first handle portion, the first actuator is a second handle portion slidably engaged to the first handle portion and the second actuator is a third handle portion slidably engaged to the second handle portion.

9. The snare of claim 6 wherein the sheath is sized to be slidably received within a working channel of an endoscope.

10. The snare of claim 6 wherein the sheath is fixedly engaged to a first handle portion.

11. The snare of claim 10 wherein the first actuator is a second handle portion slidably engaged to the first handle portion.

12. The snare of claim 10 comprising a second actuator coupled to a proximal end of the wire, the second actuator having a first position and a second position, wherein when the second actuator is in its first position, the wire is in its first position, wherein when the second actuator is in its second position, the wire is in its second position, and wherein the second actuator is a third handle portion slidably engaged to a second handle portion.

13. The snare of claim 1 wherein the snare is configured for insertion into an endoscope.

14. The snare of claim 1 wherein the snare is configured to be energized by an electrosurgical generator.

15. A snare for retrieving foreign objects within the body of a patient, the snare comprising:
    a sheath extending from a proximal end which, in an operative position, is located outside the body, to a distal end which, in the operative position is located within the body, the sheath having an outer surface and an inner surface, the inner surface defining a lumen;
    a hollow elongate tubular member disposed within the lumen of the sheath, the hollow elongate tubular member comprising an inner surface, an outer surface, a lumen defined by the inner surface, a proximal end, and a distal end, the hollow elongate tubular member forming a loop at the distal end, the loop comprising at least one opening, the loop having an open position and a closed position;
    a wire slidably disposed in the lumen of the elongate tubular member, a distal end of the wire comprising at least one engaging member for engaging tissue, the wire having a first position and a second position within the hollow elongate tubular member, wherein when the wire is in the first position the at least one engaging member extends out of the at least one opening in the hollow elongate tubular member, and wherein when the wire is in the second position, the at least one engaging member is retracted within the lumen of the hollow elongate member.

16. The snare of claim 15 further comprising a first actuator coupled to the proximal end of the hollow elongate tubular member, the first actuator having a first position and a second position, wherein when the first actuator is in the first position, the loop of the hollow elongate tubular member is disposed within the distal end of the sheath, and wherein when the first actuator is in the second position, the loop of the hollow elongate tubular member extends outside the distal end of the sheath.

17. The snare of claim 15 further comprising a second actuator coupled to a proximal end of the wire, the second actuator having a first position and a second position, wherein when the second actuator is in its first position, the at least one engaging member extends out of the at least one opening of the hollow elongate tubular member, and wherein when the second actuator is in its second position, the at least one engaging member is retracted within the lumen of the hollow elongate tubular member.

18. The snare of claim 15 wherein the proximal end of the sheath is coupled to a first handle.

19. The snare of claim 18 wherein a first actuator for actuating the hollow elongate tubular member is a second handle slidably engaged to said first handle.

20. The snare of claim 19 wherein a second actuator for the wire is a third handle slidably engaged to said second handle.

21. The snare of claim 15 wherein the snare is configured to be energized with an electrosurgical generator.

22. A snare for retrieving foreign objects within the body of a patient, the snare comprising:
- a first handle portion;
- a sheath having a proximal end, a distal end, an inner surface, and an outer surface, the inner surface defining a lumen, the sheath engaged to the first handle portion at the proximal end, wherein the distal end in an operative position of the sheath is located inside the body of a patient, and wherein the proximal end in the operative position is located outside the body of the patient;
- a second handle portion slidably engaged with the first handle portion, the second handle portion having a first position and a second position;
- a hollow elongate tubular member comprising an inner surface, an outer surface, a lumen defined by the inner surface, a proximal end, and a distal end, the hollow elongate tubular member forming a loop at its distal end, the loop comprising at least one opening, the loop having an open position and a closed position, the hollow elongate tubular member extending through the lumen of the sheath, wherein the hollow elongate tubular member is engaged to the second handle portion, and when the second handle portion is in the first position, the hollow elongate tubular member is disposed entirely within the sheath, and wherein when the second handle portion is in the second position, the loop of the hollow elongate tubular member extends from the distal end of the sheath;
- a third handle portion slidably engaged with the second handle portion, the third handle portion having a first position and a second position; and
- a wire slidably disposed in the lumen of the elongate tubular member, the wire comprising at least one engaging member for engaging tissue, the wire having a proximal end and a distal end, wherein the wire is engaged to the third handle portion at the proximal end of the wire, wherein when the third handle portion is in the first position, the at least one engaging member extends through the at least one opening in the hollow elongate tubular member, and wherein the at least one engaging member retracts into the lumen of the hollow elongate tubular member when the third handle portion is moved to the second position.

* * * * *